United States Patent
Velasquez

(10) Patent No.: US 12,402,760 B2
(45) Date of Patent: Sep. 2, 2025

(54) TOWEL WARMING ASSEMBLY INCLUDING FRAGRANCE DOOR

(71) Applicant: Simon Velasquez, Houston, TX (US)

(72) Inventor: Simon Velasquez, Houston, TX (US)

(*) Notice: Subject to any disclaimer, the term of this patent is extended or adjusted under 35 U.S.C. 154(b) by 918 days.

(21) Appl. No.: 17/564,421

(22) Filed: Dec. 29, 2021

(65) Prior Publication Data
US 2023/0277016 A1  Sep. 7, 2023

(51) Int. Cl.
*A47K 10/06* (2006.01)
*A61L 2/04* (2006.01)

(52) U.S. Cl.
CPC ............. *A47K 10/06* (2013.01); *A61L 2/04* (2013.01)

(58) Field of Classification Search
CPC ............ A47K 10/06; A61L 2/04; D06F 58/10
See application file for complete search history.

(56) References Cited

U.S. PATENT DOCUMENTS

| | | | | |
|---|---|---|---|---|
| 3,839,622 | A * | 10/1974 | Mastin | A47K 10/06 219/508 |
| D302,460 | S | 7/1989 | Gibson | |
| 5,555,640 | A * | 9/1996 | Ou | F26B 25/066 312/249.9 |
| 5,840,589 | A * | 11/1998 | Warner, Jr. | H01L 21/74 438/505 |
| 6,046,436 | A * | 4/2000 | Hunts | A47K 10/06 219/400 |
| 6,667,464 | B2 * | 12/2003 | Ellis | A47K 10/06 219/393 |
| 6,840,589 | B2 | 1/2005 | Uri | |
| 8,058,588 | B2 * | 11/2011 | Gagas | H05B 3/0071 219/400 |
| 8,481,895 | B2 * | 7/2013 | Taylor | A47K 10/06 219/535 |
| 2002/0084730 | A1 * | 7/2002 | Uri | D06F 58/10 312/228.1 |
| 2003/0015513 | A1 * | 1/2003 | Ellis | A47K 10/06 219/393 |
| 2008/0210678 | A1 * | 9/2008 | Crane | A47K 10/06 219/392 |
| 2011/0259864 | A1 | 10/2011 | Galietti | |
| 2018/0320303 | A1 * | 11/2018 | Valzelli | D06F 58/10 |
| 2018/0347102 | A1 * | 12/2018 | Um | D06F 58/10 |
| 2018/0347103 | A1 * | 12/2018 | Lee | D06F 29/005 |
| 2019/0024288 | A1 * | 1/2019 | Nam | D06F 37/26 |
| 2019/0085493 | A1 * | 3/2019 | Magnusson | D06F 18/00 |
| 2019/0100866 | A1 * | 4/2019 | Mangan | D06F 58/26 |
| 2019/0211497 | A1 * | 7/2019 | Kim | D06F 73/02 |
| 2019/0257025 | A1 * | 8/2019 | Park | D06F 71/36 |

(Continued)

*Primary Examiner* — John P. Dulka

(57) ABSTRACT

A towel warming assembly includes a housing that has an entry extending into an interior of the housing to facilitate one or more towels to be positioned within the housing. A blower is positioned in the housing to blow air into the housing such that the towels are exposed to the air blown by the blower. A heating unit is positioned in the housing to heat air blown by the blower thereby facilitating the towels to be warmed. A control unit is positioned in the electronics space in the housing and the control unit is in communication with the blower and the heating unit. The control unit includes an electronic timer and each of the blower and the heating unit is turned off when the electronic timer counts down the pre-determined duration of time.

13 Claims, 6 Drawing Sheets

(56) References Cited

U.S. PATENT DOCUMENTS

| | | | | |
|---|---|---|---|---|
| 2020/0080254 A1* | 3/2020 | Chang | ............... | D06F 39/083 |
| 2020/0375412 A1* | 12/2020 | Wallander | ............ | A61M 21/00 |
| 2021/0032797 A1* | 2/2021 | Shin | ............... | D06F 67/005 |
| 2021/0047772 A1* | 2/2021 | Jang | ............... | D06F 58/10 |
| 2021/0208590 A1* | 7/2021 | Cho | ............... | G07F 17/20 |
| 2021/0372030 A1* | 12/2021 | Kang | ............... | D06F 58/203 |
| 2022/0074123 A1* | 3/2022 | Jang | ............... | D06F 58/24 |
| 2022/0259794 A1* | 8/2022 | Kim | ............... | D06F 58/44 |
| 2023/0277016 A1* | 9/2023 | Velasquez | ............... | A61L 2/04 |
| | | | | 34/329 |
| 2023/0399789 A1* | 12/2023 | Aneladasu | ............ | D06F 58/26 |
| 2024/0167217 A1* | 5/2024 | Jang | ............... | D06F 71/34 |
| 2024/0301613 A1* | 9/2024 | Han | ............... | D06F 58/10 |
| 2025/0043501 A1* | 2/2025 | Chong | ............... | D06F 57/00 |
| 2025/0044026 A1* | 2/2025 | Wallander | ............ | F24H 3/0411 |
| 2025/0066976 A1* | 2/2025 | Lee | ............... | D06F 39/14 |
| 2025/0066980 A1* | 2/2025 | Park | ............... | D06F 39/083 |
| 2025/0066985 A1* | 2/2025 | Park | ............... | D06F 43/081 |
| 2025/0116057 A1* | 4/2025 | Kim | ............... | A61L 2/06 |

\* cited by examiner

TOWEL WARMING ASSEMBLY INCLUDING FRAGRANCE DOOR

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to warming devices and more particularly pertains to a new warming device for warming towel and imparting a pleasing fragrance into the towels. The device includes a housing and hangers in the housing for suspending towels on the hangers. The device includes a blower and heating unit for blowing heated air into the housing. Additionally, the device includes a fragrance pad, infused with a chemical fragrance, for releasing the chemical fragrance into the towels.

(2) Description of Related Art Including Information Disclosed Under 37 CFR 1.97 and 1.98

The prior art relates to warming devices a variety of towel warming chambers which each at least includes a blower and a heating element for blowing warmed air into the warming chamber for warming towels. The prior art discloses a towel warmer which includes a heating coil against which towels can be positioned for warming the towels. The prior art discloses a towel and garment warmer that includes a chamber for holding towels and garments, a heat source for warming the towels and garments and a cooling unit for cooling the towels and garments. The prior art discloses a towel warmer that includes a heating unit and a UV light emitter for warming towels.

BRIEF SUMMARY OF THE INVENTION

An embodiment of the disclosure meets the needs presented above by generally comprising a housing that has an entry extending into an interior of the housing to facilitate one or more towels to be positioned within the housing. A blower is positioned in the housing to blow air into the housing such that the towels are exposed to the air blown by the blower. A heating unit is positioned in the housing to heat air blown by the blower thereby facilitating the towels to be warmed. A control unit is positioned in the electronics space in the housing and the control unit is in communication with the blower and the heating unit. The control unit includes an electronic timer and each of the blower and the heating unit is turned off when the electronic timer counts down the pre-determined duration of time.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
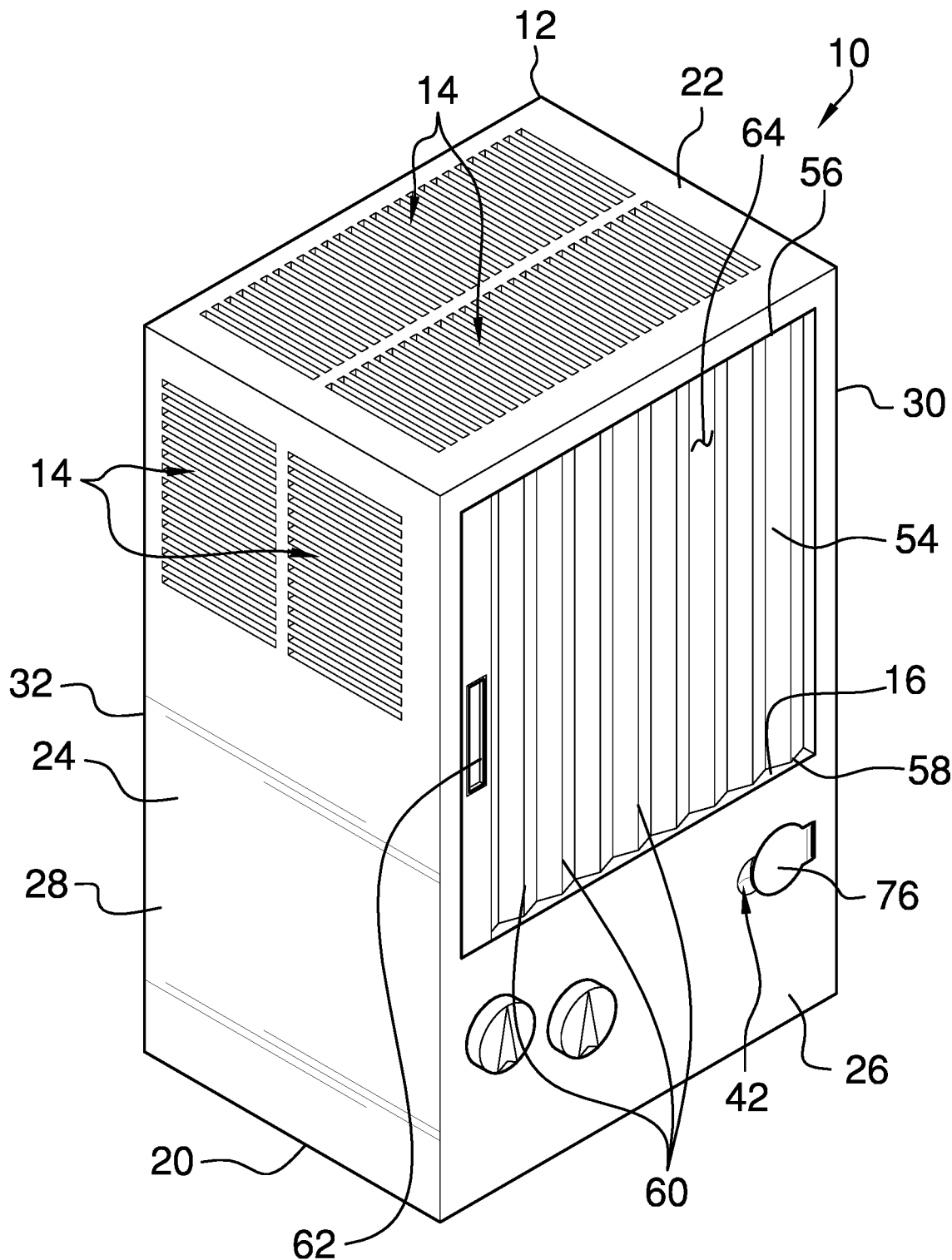
FIG. 1 is a top perspective view of a towel warming assembly according to an embodiment of the disclosure.
Figure 2:
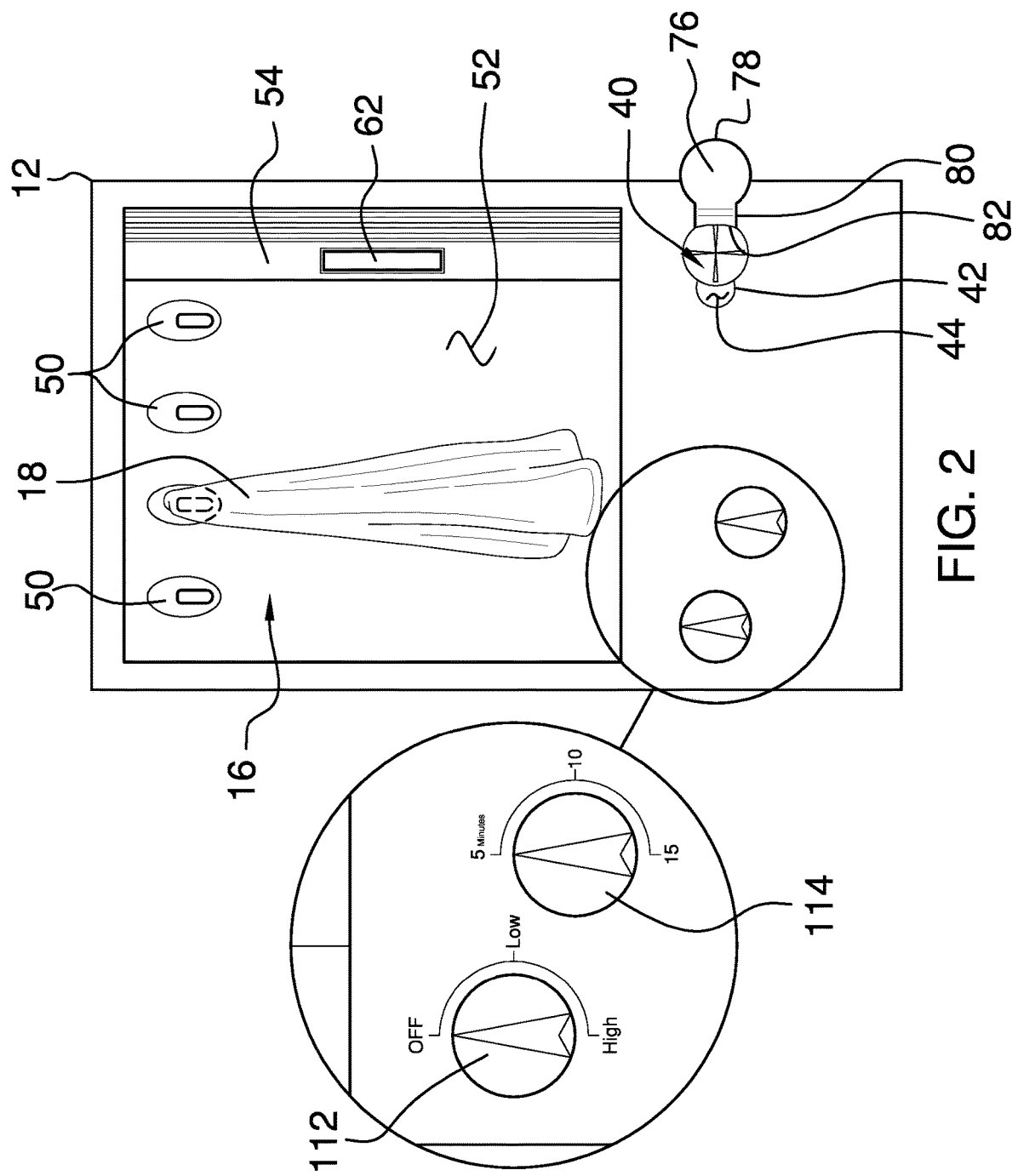
FIG. 2 is a front view of an embodiment of the disclosure.
Figure 3:
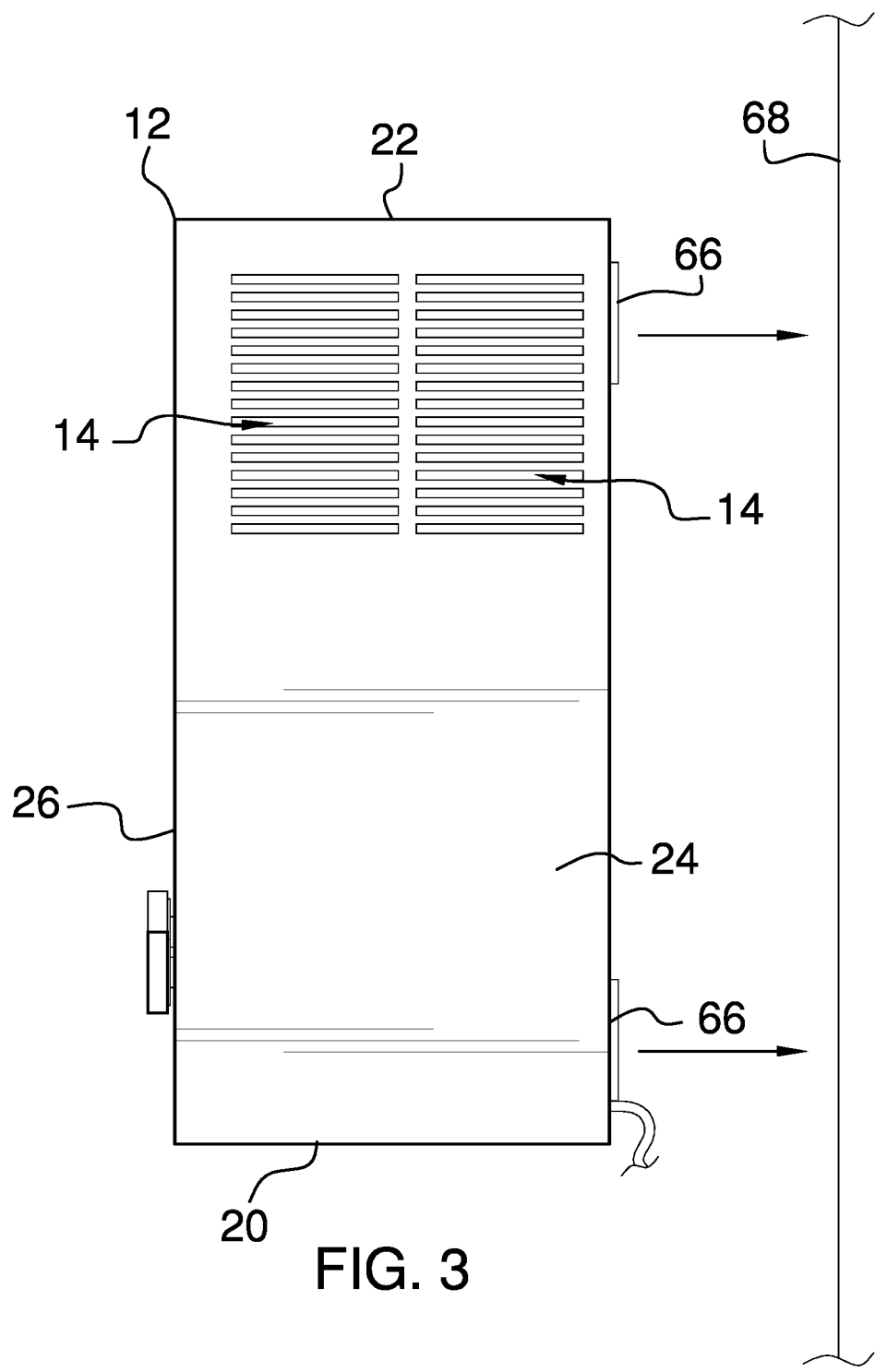
FIG. 3 is a left side view of an embodiment of the disclosure.
Figure 4:
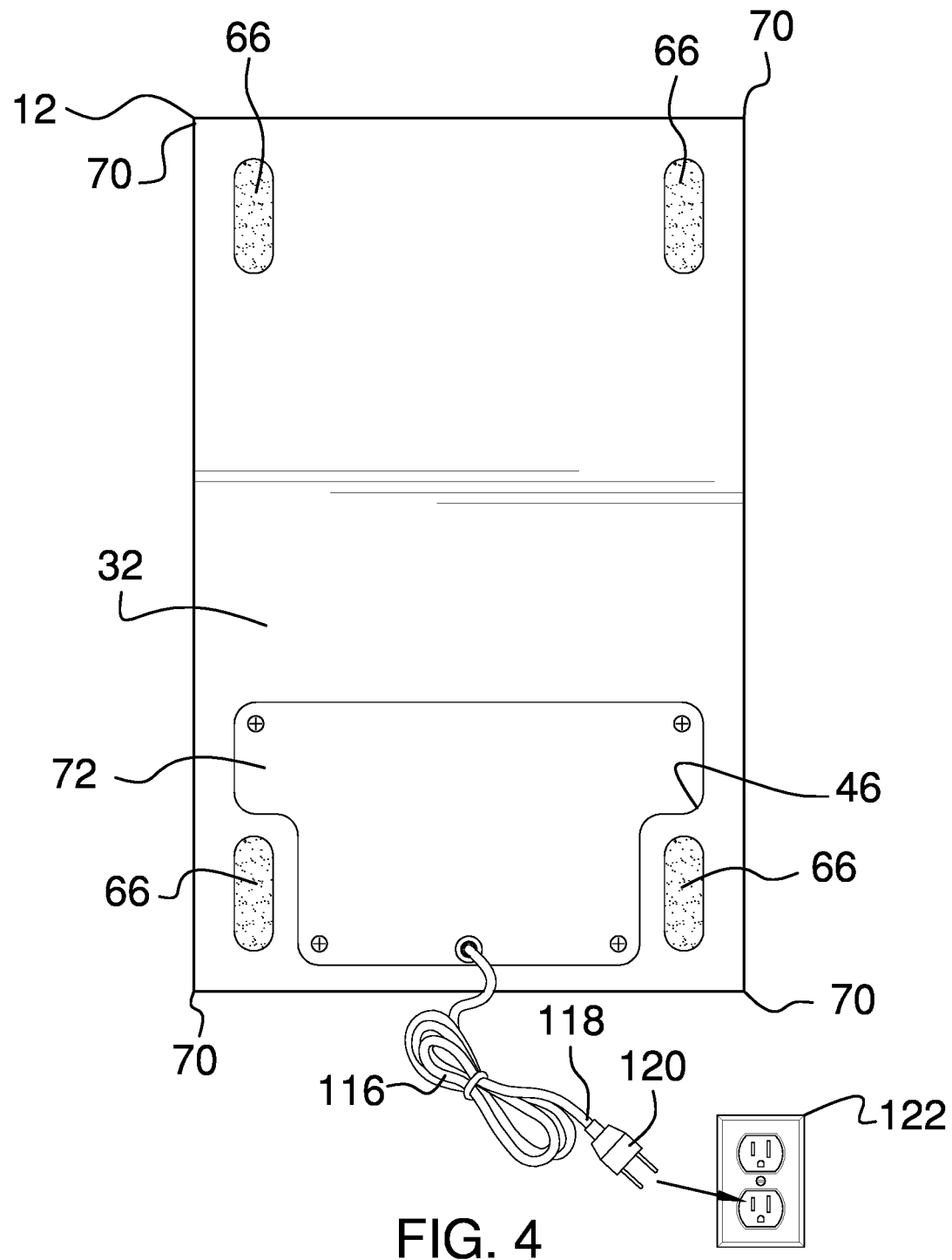
FIG. 4 is a back view of an embodiment of the disclosure.
Figure 5:
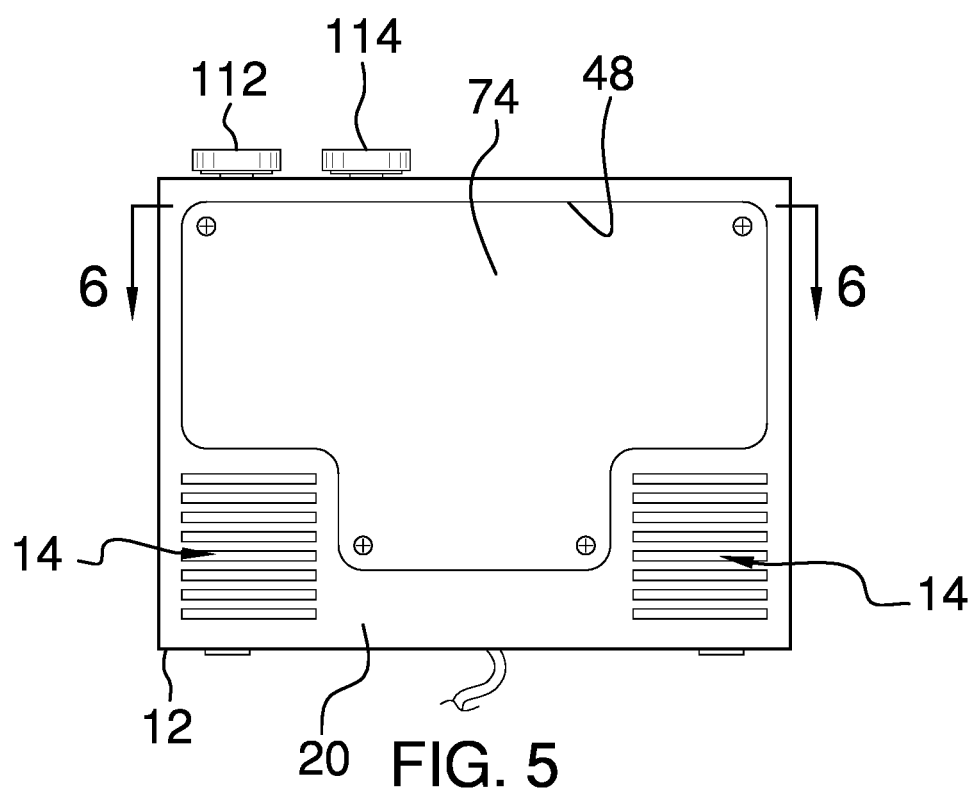
FIG. 5 is a bottom view of an embodiment of the disclosure.
Figure 6:
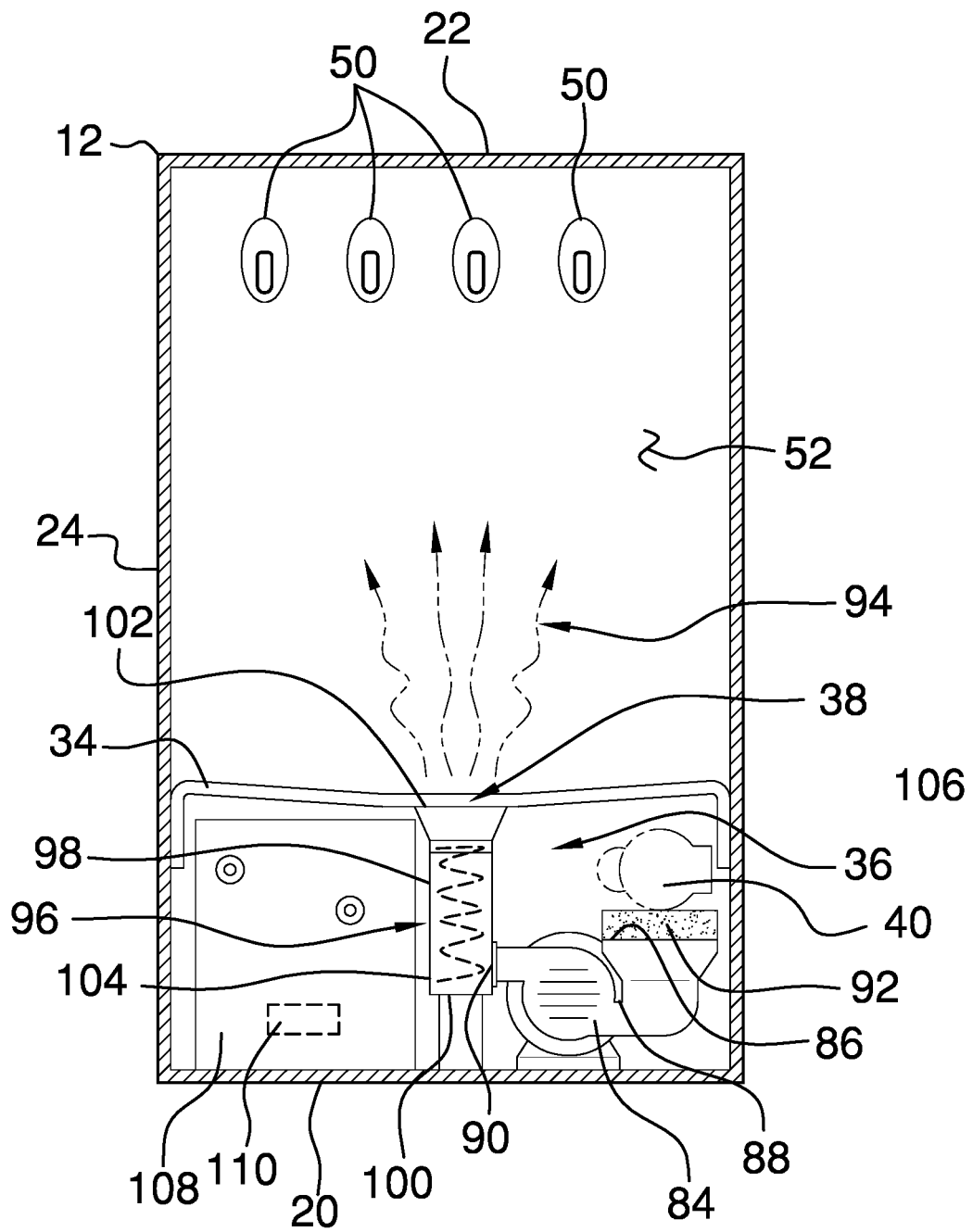
FIG. 6 is a cross sectional view taken along line 6-6 of FIG. 5 of an embodiment of the disclosure.

With reference now to the drawings, and in particular to FIGS. 1 through 6 thereof, a new warming device embodying the principles and concepts of an embodiment of the disclosure and generally designated by the reference numeral 10 will be described.

As best illustrated in FIGS. 1 through 6, the towel warming assembly 10 generally comprises a housing 12 that has a plurality of vents 14 each extending into an interior of the housing 12 to pass air into the housing 12. The housing 12 has an entry 16 extending into an interior of the housing 12 to facilitate one or more towels 18 to be positioned within the housing 12. The towels 18 may be bathing towels or other types of towels that would commonly be employed for bathing or the like. The housing 12 has a bottom wall 20, a top wall 22 and an outer wall 24 extending between the top wall 22 and the bottom wall 20, and the outer wall 24 has a front side 26, a first lateral side 28, a second lateral side 30 and a back side 32. Each of the plurality of vents 14 extends through a respective one of the top wall 22, the first lateral side 28, the second lateral side 30 and the bottom wall 20, and the entry 16 extends through the front side 26. Additionally, the entry 16 extends through the front side 26 and the entry 16 is positioned closer to the top wall 22 than the bottom wall 20.

The housing 12 has a divider 34 that is positioned between the top wall 22 and the bottom wall 20 to define an electronics space 36 between the bottom wall 20 and the divider 34. The divider 34 is positioned closer to the bottom wall 20 than the top wall 22 and the divider 34 has an air opening 38 extending through the divider 34. The front side 26 has a fragrance opening 40 extending into the electronics space 36 and the fragrance opening 40 is positioned between the entry 16 and the bottom wall 20. The fragrance opening 40 is positioned adjacent to the second lateral side 30 of the outer wall 24.

The front side 26 has a depression 42 extending into the front side 26 and the depression 42 has a bounding surface 44. The bounding surface 44 is concavely arcuate with respect to the front side 26 and the depression 42 is positioned adjacent to the fragrance opening 40. The back side 32 has a first electronics opening 46 extending into the electronics space 36. Additionally, the bottom wall 20 has a second electronics opening 48 extending into the electronics space 36.

A plurality of hangers 50 is each positioned within the housing 12 and each of the hangers 50 can have a respective towel 18 hung from the hangers 50. Each of the hangers 50 is positioned on an inside surface 52 of the back side 32 of the outer wall 24 of the housing 12. Furthermore, each of the hangers 50 is positioned adjacent to the top wall 22. The hangers 50 are spaced apart from each other and are distributed between the first lateral side 28 and the second lateral side 30 of the outer wall 24 of the housing 12.

A door 54 is provided and the door 54 is slidably disposed in the entry 16. The door 54 is positionable in a closed position having the door 54 closing the entry 16. Conversely, the door 54 is positionable in an open position having the door 54 exposing the entry 16. The door 54 has a top edge 56 and a bottom edge 58, and the door 54 has a plurality of pleats 60 each extending between the top edge 56 and the bottom edge 58. The door 54 is foldable along each of the pleats 60 thereby collapsing the door 54 into the closed position. Furthermore, the door 54 is un-foldable along each of the pleats 60 thereby expanding the door 54 into the open position. A grip 62 is disposed on a front surface 64 of the door 54 for gripping to urge the door 54 between the open position and the closed position.

A plurality of mating units 66 is provided and each of the mating units 66 is coupled to the back side 32 of the outer wall 24 of the housing 12. In this way each of the mating units 66 can engage a vertical support surface 68 for suspending the housing 12 on the vertical support surface 68. The vertical support surface 68 may be a wall of a room or other similar vertical support surface 68. Each of the mating units 66 is aligned with a respective one of four corners 70 of the back side 32.

A first panel 72 is removably attached to the back side 32 of the outer wall 24 and the first panel 72 covers the first electronics opening 46. A second panel 74 is removably attached to the bottom wall 20 of the housing 12 and the second panel 74 covers the second electronics opening 48. A fragrance door 76 is hingedly coupled to the front side 26 of the outer wall 24 of the housing 12 and the fragrance door 76 is aligned with the fragrance opening 40 in the front side 26 of the outer wall 24. The fragrance door 76 has a perimeter edge 78 and the perimeter edge 78 is continuously arcuate such that the fragrance door 76 has a circular shape. The fragrance door 76 has a tab 80 extending away from the perimeter edge 78, the tab 80 has a distal end 82 with respect to the perimeter edge 78 and the distal end 82 is hingedly coupled to the front side 26.

The fragrance door 76 covers the fragrance opening 40 when the fragrance door 76 is closed. Conversely, the fragrance door 76 exposes the fragrance opening 40 when the fragrance door 76 is closed. The perimeter edge 78 is aligned with the depression 42 in the front side 26 of the outer wall 24 of the housing 12. In this way the depression 42 facilitates a user to grip 62 the perimeter edge 78 for opening the fragrance door 76.

A blower 84 is positioned in the housing 12 to blow air into the housing 12 such that the towels 18 are exposed to the air blown by the blower 84. The blower 84 is positioned in the electronics space 36 and the blower 84 has a fragrance port 86 which is integrated into the blower 84. The blower 84 has an intake 88 and an exhaust 90, and the blower 84 urges air inwardly into the intake 88 and outwardly through the exhaust 90 when the blower 84 is turned on. The fragrance port 86 is in fluid communication with the intake 88 and the fragrance port 86 is aligned with the fragrance opening 40 in the front side 26 of the outer wall 24 of the housing 12. In this way a fragrance pad 92 can be positioned on the fragrance port 86. The fragrance pad 92 is infused with a chemical fragrance 94 to facilitate the chemical fragrance 94 to be released into the air blown by the blower 84. In this way the chemical fragrance 94 can be distributed onto the towels 18 in the housing 12 thereby imparting a pleasing aroma into the towels 18.

A heating unit 96 is provided and the heating unit 96 is positioned in the housing 12. The heating unit 96 is in fluid communication with the blower 84 such that the heating unit 96 heats air blown by the blower 84 thereby facilitating the towels 18 to be warmed. The heating unit 96 comprises a tube 98 that has a lower end 100, an upper end 102 and an exterior wall 104 extending between the lower end 100 and the upper end 102. The exterior wall 104 is fluidly coupled to the exhaust 90 of the blower 84 at a point that is located adjacent to the lower end 100. In this way the tube 98 can receive the air blown by the blower 84. The upper end 102 is coupled to the divider 34 having the upper end 102 being aligned with the air opening 38 in the divider 34. In this way the tube 98 can direct the air blown by the blower 84 through the air opening 38.

The heating unit 96 includes a heating element 106 that is disposed within the tube 98. The heating element 106 generates heat when the heating element 106 is turned on. In this way the heating element 106 can heat the air is blown through the tube 98. The heating element 106 may comprise an electric heating element or the like and the heating element 106 may have an operational temperature ranging between approximately 100.0 degrees Fahrenheit and 180.0 degrees Fahrenheit.

A control unit 108 is positioned in the electronics space 36 in the housing 12 and the control unit 108 is in communication with the blower 84 and the heating unit 96. The control unit 108 includes an electronic timer 110 and the electronic timer 110 is in communication with each of the blower 84 and the heating unit 96. The electronic timer 110 counts down a pre-determined duration of time ranging between a minimum duration of time and a maximum duration of time. Furthermore, each of the blower 84 and the heating unit 96 is turned off when the electronic timer 110 counts down the pre-determined duration of time. The blower 84 is electrically coupled to the control unit 108, the heating element 106 is electrically coupled to the control unit 108 and the control unit 108 is positioned within the electronics space 36 in the housing 12.

A power knob 112 is rotatably coupled to the housing 12 such that the power knob 112 can be manipulated by a user. The power knob 112 is positionable in an off position, a low position or a high position. Each of the blower 84 and the heating unit 96 is turned off when the power knob 112 is positioned in the off position. Each of the blower 84 and the heating unit 96 is actuated into a minimum intensity when the power knob 112 is positioned in the low position. Additionally, each of the blower 84 and the heating unit 96 is actuated into a maximum intensity when the power knob 112 is positioned in the high position. The power knob 112 is positioned on the front side 26 of the outer wall 24 of the housing 12 and the power knob 112 is positioned between the entry 16 and the bottom wall 20 of the housing 12. Additionally, the power knob 112 is operationally coupled to the control unit 108.

A timer knob 114 is rotatably coupled to the housing 12 such that the timer knob 114 can be manipulated by a user. The timer knob 114 is positionable in a minimum position, a medial position or a maximum position. The electronic timer 110 counts down a minimum duration of time when the timer knob 114 is in the minimum position, which may be approximately five minutes. The electronic timer 110 counts down a medial duration of time when the timer knob 114 is in the medial position, which may be approximately ten minutes. Continuing, the electronic timer 110 counts down a maximum duration of time when the timer knob 114 is in the maximum position, which may be approximately fifteen minutes. The timer knob 114 is positioned on the front side 26 of the outer wall 24 of the housing 12, and the timer knob 114 is positioned between the entry 16 and the bottom wall 20. Additionally, the timer knob 114 is operationally coupled to the control unit 108.

A power cord 116 is coupled to and extends away from the back side 32 of the outer wall 24 of the housing 12 and the power cord 116 is electrically coupled to the control unit 108. The power cord 116 has a distal end 118 with respect to the back side 32 and a male plug 120 is electrically coupled to the distal end 118. The male plug 120 can be plugged into a power source 122 comprising a female electrical outlet.

In use, the towels 18 are suspended on a respective hanger and the door 54 is positioned in the closed position. The power knob 112 is positioned in either the low position or the high position, depending on the user's preference, and the timer knob 114 is positioned in either the minimum position, the medial position or the maximum position, depending on the user's preference. In this way the blower 84 and the heating unit 96 are turned on to blow heated air into the housing 12 to warm the towels 18. Additionally, the fragrance pad 92 imparts a pleasing aroma into the towels 18. In this way the towels 18 are warmed and have a pleasing aroma when the towels 18 are employed for drying off after bathing, for example. The fragrance pad 92 can be replaced when the chemical fragrance 94 in the fragrance pad 92 is depleted.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A towel warming assembly comprising:
a housing having a plurality of vents each extending into an interior of said housing wherein each of said vents is configured to pass air into said housing, said housing having an entry extending into said interior of said housing wherein said entry is configured to facilitate a plurality of towels to be positioned within said housing, said housing having a bottom wall, a top wall and an outer wall extending between said top wall and said bottom wall, said outer wall having a front side, a first lateral side, a second lateral side and a back side, said front side having a fragrance opening;
a plurality of hangers, each of said hangers being positioned within said housing wherein each of said hangers is configured to have an associated towel of the plurality of towels to be hung from said hanger;
a door being slidably disposed in said entry, said door being positionable in a closed position having said door closing said entry, said door being positionable in an open position having said door exposing said entry;
a fragrance door being hingedly coupled to said front side of said outer wall of said housing, said fragrance door being aligned with said fragrance opening in said front side of said outer wall for opening and closing said fragrance opening;
a blower being positioned in said housing wherein said blower is configured to blow air into said housing such that the plurality of towels is exposed to the air blown by said blower;
a heating unit being positioned in said housing, said heating unit being in fluid communication with said blower wherein said heating unit is configured to heat air being blown by said blower thereby facilitating the plurality of towels to be warmed; and
a control unit being positioned in said housing, said control unit being in communication with said blower and said heating unit, said control unit including an electronic timer, said electronic timer being in communication with each of said blower and said heating unit, said electronic timer counting down a pre-determined duration of time ranging between a minimum duration of time and a maximum duration of time, each of said blower and said heating unit being turned off when said electronic timer counts down said pre-determined duration of time.

2. The assembly according to claim 1, wherein:
each of said plurality of vents extends through a respective one of said top wall, said first lateral side, said second lateral side and said bottom wall, said entry extending through said front side;
said housing having a divider being positioned between said top wall and said bottom wall to define an electronics space between said bottom wall and said divider, said divider being positioned closer to said bottom wall than said top wall, said divider having an air opening extending through said divider;

said entry extends through said front side, said entry being positioned closer to said top wall than said bottom wall;

said fragrance opening extending into said electronics space, said fragrance opening being positioned between said entry and said bottom wall, said fragrance opening being positioned adjacent to said second lateral side of said outer wall;

said front side has a depression extending into said front side, said depression having a bounding surface, said bounding surface being concavely arcuate with respect to said front side, said depression being positioned adjacent to said fragrance opening;

said back side has a first electronics opening extending into said electronics space; and said bottom wall has a second electronics opening extending into said electronics space.

3. The assembly according to claim 2, wherein each of said hangers is positioned on an inside surface of said back side of said outer wall of said housing, each of said hangers being positioned adjacent to said top wall, said hangers being spaced apart from each other and being distributed between said first lateral side and said second lateral side of said outer wall of said housing.

4. The assembly according to claim 2, further comprising a plurality of mating units, each of said mating units being coupled to said back side of said outer wall of said housing wherein each of said mating units is configured to engage a vertical support surface for suspending said housing on the vertical support surface, each of said mating units being aligned with a respective one of four corners of said back side.

5. The assembly according to claim 2, further comprising:
a first panel being removably attached to said back side of said outer wall, said first panel covering said first electronics opening; and
a second panel being removably attached to said bottom wall of said housing, said second panel covering said second electronics opening.

6. The assembly according to claim 2, wherein said fragrance door has a perimeter edge, said perimeter edge being continuously arcuate such that said fragrance door has a circular shape, said fragrance door having a tab extending away from said perimeter edge, said tab having a distal end with respect to said perimeter edge, said distal end being hingedly coupled to said front side, said fragrance door covering said fragrance opening when said fragrance door is closed, said fragrance door exposing said fragrance opening when said fragrance door is closed, said perimeter edge being aligned with said depression in said front side of said outer wall of said housing wherein said depression is configured to facilitate a user to grip said perimeter edge for opening said fragrance door.

7. The assembly according to claim 2, wherein:
said blower is positioned in said electronics space, said blower having a fragrance port being integrated into said blower, said blower having an intake and an exhaust wherein said blower is configured to urge air inwardly into said intake and outwardly through said exhaust; and
said fragrance port is in fluid communication with said intake, said fragrance port being aligned with said fragrance opening in said front side of said outer wall of said housing thereby facilitating a fragrance pad to be positioned on said fragrance port, said fragrance pad being infused with a chemical fragrance wherein said fragrance pad is configured to facilitate the chemical fragrance to be released into the air blown by said blower thereby facilitating the chemical fragrance to be distributed onto the plurality of towels in said housing thereby imparting a pleasing aroma into the plurality of towels.

8. The assembly according to claim 7, wherein said heating unit comprises:
a tube having a lower end, an upper end and an exterior wall extending between said lower end and said upper end, said exterior wall being fluidly coupled to said exhaust of said blower at a point being located adjacent to said lower end wherein said tube is configured to receive the air blown by said blower, said upper end being coupled to said divider having said upper end being aligned with said air opening in said divider wherein said tube is configured to direct the air blown by said blower through said air opening; and
a heating element being disposed within said tube, said heating element generating heat when said heating element is turned on wherein said heating element is configured to heat the air being blown through said tube.

9. The assembly according to claim 2, wherein:
said assembly includes a power knob being rotatably coupled to said housing wherein said power knob is configured to be manipulated by a user, said power knob being positionable in an off position, a low position or a high position, each of said blower and said heating unit being turned off when said power knob is positioned in said off position, each of said blower and said heating unit being actuated into a minimum intensity when said power knob is positioned in said low position, each of said blower and said heating unit being actuated into a maximum intensity when said power knob is positioned in said high position; and
said power knob is positioned on said front side of said outer wall of said housing, said power knob being positioned between said entry and said bottom wall of said housing, said power knob being operationally coupled to said control unit.

10. The assembly according to claim 2, wherein:
said assembly includes a timer knob being rotatably coupled to said housing wherein said timer knob is configured to be manipulated by a user, said timer knob being positionable in a minimum position, a medial position or a maximum position, said electronic timer counting down a minimum duration of time when said timer knob is in said minimum position, said electronic timer counting down a medial duration of time when said timer knob is in said medial position, said electronic timer counting down a maximum duration of time when said timer knob is in said maximum position; and
said timer knob is positioned on said front side of said outer wall of said housing, said timer knob being positioned between said entry and said bottom wall, said timer knob being operationally coupled to said control unit.

11. The assembly according to claim 2, further comprising a power cord being coupled to and extending away from said back side of said outer wall of said housing, said power cord being electrically coupled to said control unit, said power cord having a distal end with respect to said back side, said distal end having a male plug being electrically coupled to said distal end wherein said male plug is configured to be plugged into a power source comprising a female electrical outlet.

12. The assembly according to claim 1, wherein;
   said door has a top edge and a bottom edge, said door having a plurality of pleats each extending between said top edge and said bottom edge, said door foldable along each of said pleats thereby collapsing said door into said closed position, said door being un-foldable along each of said pleats thereby expanding said door into said open position; and
   said assembly includes a grip being disposed on a front surface of said door wherein said grip is configured to be gripped for urging said door between said open position and said closed position.

13. A towel warming assembly comprising:
   a housing having a plurality of vents each extending into an interior of said housing wherein each of said vents is configured to pass air into said housing, said housing having an entry extending into an interior of said housing wherein said entry is configured to facilitate a plurality of towels to be positioned within said housing, said housing having a bottom wall, a top wall and an outer wall extending between said top wall and said bottom wall, said outer wall having a front side, a first lateral side, a second lateral side and a back side, each of said plurality of vents extending through a respective one of said top wall, said first lateral side, said second lateral side and said bottom wall, said entry extending through said front side, said housing having a divider being positioned between said top wall and said bottom wall to define an electronics space between said bottom wall and said divider, said divider being positioned closer to said bottom wall than said top wall, said divider having an air opening extending through said divider, said entry extending through said front side, said entry being positioned closer to said top wall than said bottom wall, said front side having a fragrance opening extending into said electronics space, said fragrance opening being positioned between said entry and said bottom wall, said fragrance opening being positioned adjacent to said second lateral side of said outer wall, said front side having a depression extending into said front side, said depression having a bounding surface, said bounding surface being concavely arcuate with respect to said front side, said depression being positioned adjacent to said fragrance opening, said back side having a first electronics opening extending into said electronics space, said bottom wall having a second electronics opening extending into said electronics space;
   a plurality of hangers, each of said hangers being positioned within said housing wherein each of said hangers is configured to have an associated towel of said plurality of towels to be hung from said hanger, each of said hangers being positioned on an inside surface of said back side of said outer wall of said housing, each of said hangers being positioned adjacent to said top wall, said hangers being spaced apart from each other and being distributed between said first lateral side and said second lateral side of said outer wall of said housing;
   a door being slidably disposed in said entry, said door being positionable in a closed position having said door closing said entry, said door being positionable in an open position having said door exposing said entry, said door having a top edge and a bottom edge, said door having a plurality of pleats each extending between said top edge and said bottom edge, said door foldable along each of said pleats thereby collapsing said door into said closed position, said door being un-foldable along each of said pleats thereby expanding said door into said open position;
   a grip being disposed on a front surface of said door wherein said grip is configured to be gripped for urging said door between said open position and said closed position;
   a plurality of mating units, each of said mating units being coupled to said back side of said outer wall of said housing wherein each of said mating units is configured to engage a vertical support surface for suspending said housing on the vertical support surface, each of said mating units being aligned with a respective one of four corners of said back side;
   a first panel being removably attached to said back side of said outer wall, said first panel covering said first electronics opening;
   a second panel being removably attached to said bottom wall of said housing, said second panel covering said second electronics opening;
   a fragrance door being hingedly coupled to said front side of said outer wall of said housing, said fragrance door being aligned with said fragrance opening in said front side of said outer wall, said fragrance door having a perimeter edge, said perimeter edge being continuously arcuate such that said fragrance door has a circular shape, said fragrance door having a tab extending away from said perimeter edge, said tab having a distal end with respect to said perimeter edge, said distal end being hingedly coupled to said front side, said fragrance door covering said fragrance opening when said fragrance door is closed, said fragrance door exposing said fragrance opening when said fragrance door is closed, said perimeter edge being aligned with said depression in said front side of said outer wall of said housing wherein said depression is configured to facilitate a user to grip said perimeter edge for opening said fragrance door;
   a blower being positioned in said housing wherein said blower is configured to blow air into said housing such that the plurality of towels is exposed to the air blown by said blower, said blower being positioned in said electronics space, said blower having a fragrance port being integrated into said blower, said blower having an intake and an exhaust wherein said blower is configured to urge air inwardly into said intake and outwardly through said exhaust, said fragrance port being in fluid communication with said intake, said fragrance port being aligned with said fragrance opening in said front side of said outer wall of said housing thereby facilitating a fragrance pad to be positioned on said fragrance port, said fragrance pad being infused with a chemical fragrance wherein said fragrance pad is configured to facilitate the chemical fragrance to be released into the air blown by said blower thereby facilitating the chemical fragrance to be distributed onto the plurality of towels in said housing thereby imparting a pleasing aroma into the plurality of towels;
   a heating unit being positioned in said housing, said heating unit being in fluid communication with said blower wherein said heating unit is configured to heat air being blown by said blower thereby facilitating the plurality of towels to be warmed, said heating unit comprising:

a tube having a lower end, an upper end and an exterior wall extending between said lower end and said upper end, said exterior wall being fluidly coupled to said exhaust of said blower at a point being located adjacent to said lower end wherein said tube is configured to receive the air blown by said blower, said upper end being coupled to said divider having said upper end being aligned with said air opening in said divider wherein said tube is configured to direct the air blown by said blower through said air opening; and a heating element being disposed within said tube, said heating element generating heat when said heating element is turned on wherein said heating element is configured to heat the air being blown through said tube;

a control unit being positioned in said electronics space in said housing, said control unit being in communication with said blower and said heating unit, said control unit including an electronic timer, said electronic timer being in communication with each of said blower and said heating unit, said electronic timer counting down a pre-determined duration of time ranging between a minimum duration of time and a maximum duration of time, each of said blower and said heating unit being turned off when said electronic timer counts down said pre-determined duration of time, said blower being electrically coupled to said control unit, said heating element being electrically coupled to said control unit, said control unit being positioned within said electronics space in said housing;

a power knob being rotatably coupled to said housing wherein said power knob is configured to be manipulated by a user, said power knob being positionable in an off position, a low position or a high position, each of said blower and said heating unit being turned off when said power knob is positioned in said off position, each of said blower and said heating unit being actuated into a minimum intensity when said power knob is positioned in said low position, each of said blower and said heating unit being actuated into a maximum intensity when said power knob is positioned in said high position, said power knob being positioned on said front side of said outer wall of said housing, said power knob being positioned between said entry and said bottom wall of said housing, said power knob being operationally coupled to said control unit;

a timer knob being rotatably coupled to said housing wherein said timer knob is configured to be manipulated by a user, said timer knob being positionable in a minimum position, a medial position or a maximum position, said electronic timer counting down a minimum duration of time when said timer knob is in said minimum position, said electronic timer counting down a medial duration of time when said timer knob is in said medial position, said electronic timer counting down a maximum duration of time when said timer knob is in said maximum position, said timer knob being positioned on said front side of said outer wall of said housing, said timer knob being positioned between said entry and said bottom wall, said timer knob being operationally coupled to said control unit; and a power cord being coupled to and extending away from said back side of said outer wall of said housing, said power cord being electrically coupled to said control unit, said power cord having a distal end with respect to said back side, said distal end having a male plug being electrically coupled to said distal end wherein said male plug is configured to be plugged into a power source comprising a female electrical outlet.

* * * * *